United States Patent [19]

Fageol et al.

[11] Patent Number: 5,405,340
[45] Date of Patent: Apr. 11, 1995

[54] THREADED SECURING APPARATUS FOR FLOW CONNECTORS

[75] Inventors: Frank R. Fageol, Laurinburg, N.C.; Peter R. Kessenich, Waukegan; Mark E. Larkin, Lindenhurst, both of Ill.

[73] Assignee: Abbott Laboratories, Abbott Park, Ill.

[21] Appl. No.: 192,892

[22] Filed: Feb. 7, 1994

Related U.S. Application Data

[63] Continuation of Ser. No. 957,960, Oct. 7, 1992, abandoned.

[51] Int. Cl.⁶ .......................................... A61M 25/00
[52] U.S. Cl. ................................. 604/283; 604/240; 604/241; 604/243; 285/247; 411/431; 411/436
[58] Field of Search ............... 604/206, 240, 241, 243, 604/256, 283, 905; 285/32, 40, 25, 246, 247, 333, 332; 411/436, 437, 431, 374, 265

[56] References Cited

U.S. PATENT DOCUMENTS

| | | | |
|---|---|---|---|
| 1,317,314 | 9/1919 | Powers | 604/241 |
| 2,542,024 | 11/1970 | Burke | 604/241 |
| 2,677,373 | 5/1954 | Barradas | 604/206 |
| 2,932,305 | 4/1960 | Kirche | 285/32 |
| 3,042,737 | 7/1962 | Brumbach et al. | 285/247 |
| 3,177,016 | 4/1965 | Holmgren | 285/247 |
| 3,402,713 | 9/1968 | Senkowski et al. | 604/241 |
| 3,507,279 | 4/1970 | Senkowski | 604/241 |
| 4,079,966 | 3/1978 | Berry et al. | 285/40 |
| 4,607,868 | 8/1986 | Harvey et al. | 604/241 |
| 4,752,292 | 6/1988 | Lopez et al. | 604/244 |

Primary Examiner—C. Fred Rosenbaum
Assistant Examiner—N. Kent Gring
Attorney, Agent, or Firm—A. Nicholas Trausch

[57] ABSTRACT

A self-threading securing apparatus is used in combination with two tubular flow connectors to prevent the inadvertent disconnection of I.V. tubing sets. The securing apparatus includes a hollow shroud surrounding an extending cannula. The inner surface of the shroud includes interior threads for self-threading engagement with the resilient rolled-over exterior surface portion of the reseal connector.

8 Claims, 2 Drawing Sheets

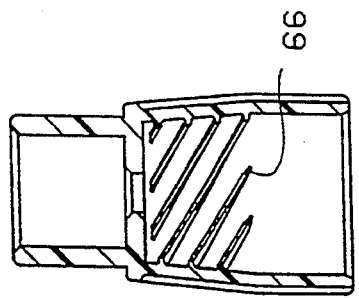
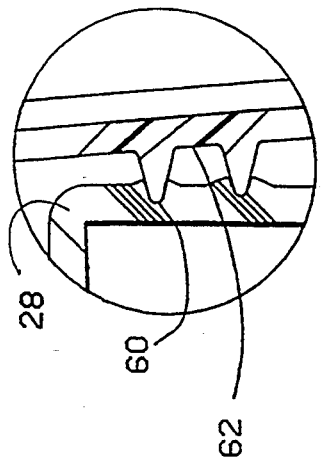
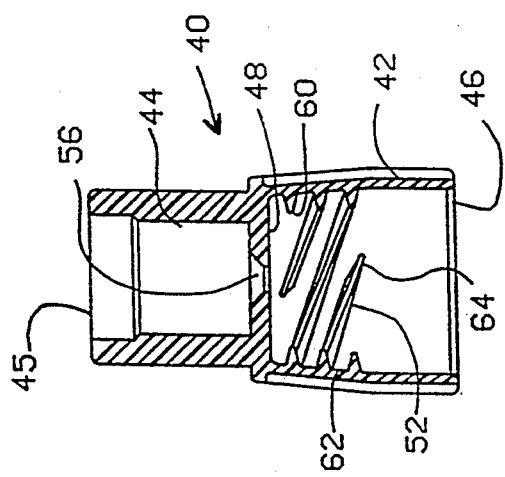
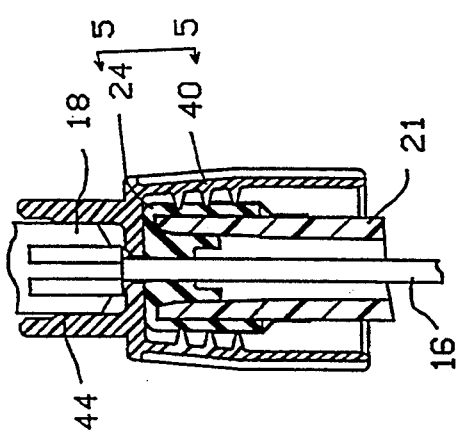
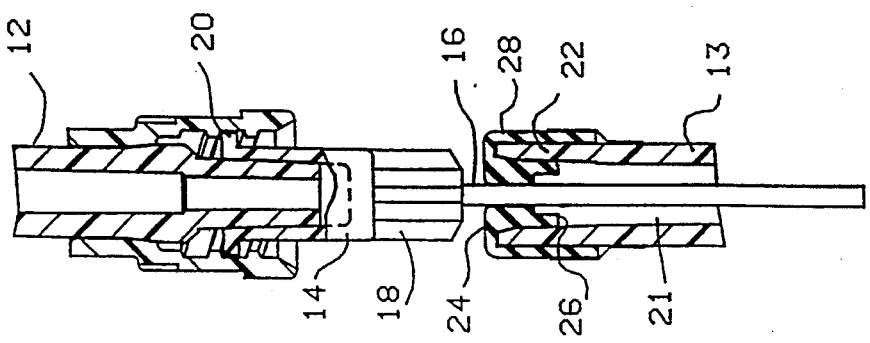

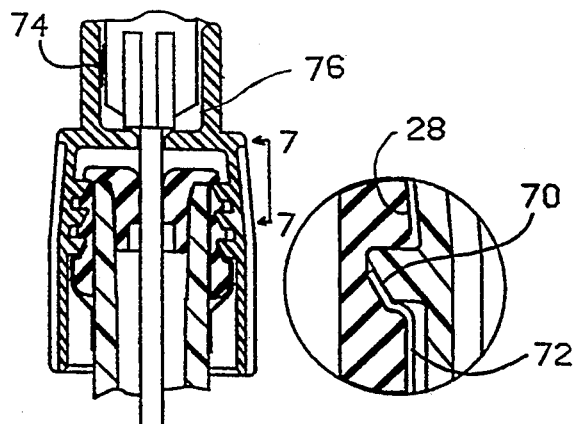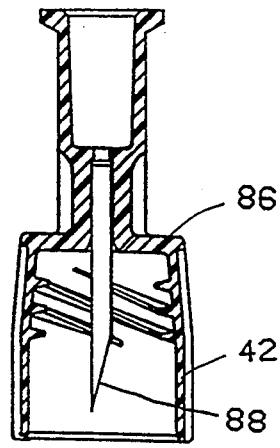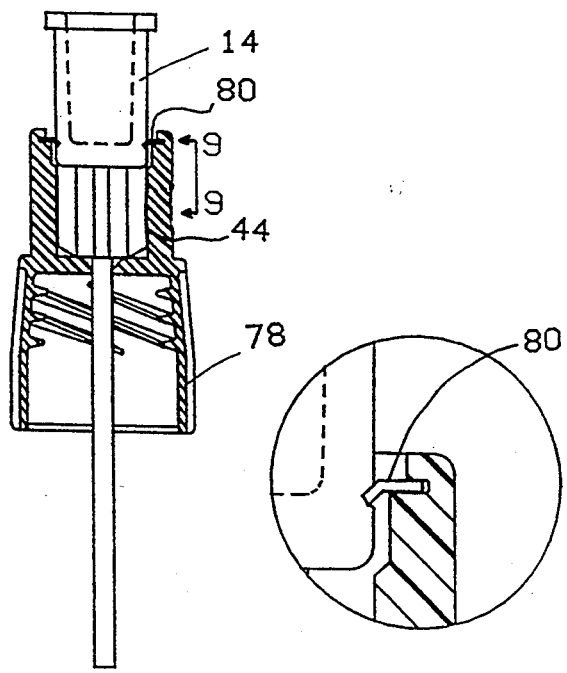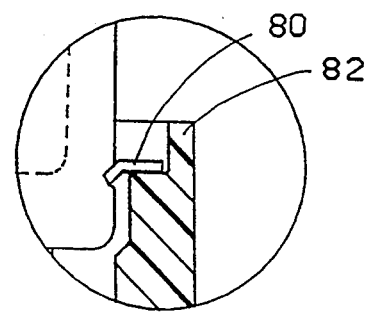

THREADED SECURING APPARATUS FOR FLOW CONNECTORS

This application is a continuation of U.S. patent application Ser. No. 07/957,960 filed Oct. 7, 1992, now abandoned.

BACKGROUND OF THE INVENTION

The present invention relates to an axial securing apparatus used to prevent the inadvertent disengagement of medical tubing sets used in intravenous therapy. More particularly, the invention relates to a self threading securing apparatus used to secure two fluid connectors together when used to sterilely transfer fluids from one IV flow conduit to a second IV flow conduit.

Intravenous therapy involves the flow of a therapeutic solution from a sterile source container to a patient's vein. At least one sterile tubing set and therefore one sterile connection are typically required to transfer the fluid from the container to the patient's vein access device. Sterile connections with intravenous tubing sets can be made in a variety ways. Connections are commonly made using sharp needle connectors with resealable elastomeric septums. Recently, due to the concerns about accidental needle sticks, blunt cannula connectors have been utilized to connect with prepierced elastomeric septums.

A primary concern with any medical tubing connector is the inadvertent disengagement of the tubing sets. An uninterrupted flow of solution to the patient is important in intravenous therapy. Also, the sterility and integrity of the flow system must be maintained. Contaminants may be introduced into the flow system if the connectors are inadvertently disengaged and are reconnected.

The above concerns have led to medical guidelines and procedures that suggest and sometimes require that I.V. connections be secured together. A variety of securing mechanisms are in use for securing I.V. connections. However, many of the known securing mechanisms are undesirable, for example, because of their bulk, complexity and/or expense, the discomfort they cause the patient, the amount of time and manipulation require from the health care provider to attach and release the securing mechanisms, or their lack of effectiveness in preventing disconnections.

Tape is often used when no suitable securing mechanism is available. However, tape has an inherent drawback when the connectors need to be quickly disconnected. Also, tape is awkward to use when one of the connectors is in close proximity to the patient's body such as at the vein access site. Any movement of the connector at the vein access site, for example, can cause patient discomfort or damage to the vein wall.

Thus, there is a need for a simple and inexpensive securing apparatus that can prevent inadvertent disengagement of tubing sets. It is desirable that the securing apparatus be readily engageable and disengagable. Further, it is desirable that the securing apparatus be easy to manipulate and compatible with many different connectors.

SUMMARY OF THE INVENTION

Therefore it is a primary object of this invention to provide a simple and reliable construction for a securing apparatus used in combination with intravenous fluid flow connectors.

It is another object of this invention to provide an axial securing apparatus for intravenous tubing connectors such as sharp needles and resealable septums, or blunt cannula and prepierced septums.

It is a further object of this invention to provide a securing apparatus that is easy to manipulate by the health care provider, yet reliable in securing the connectors of the intravenous tubing set.

In accordance with these objectives, a securing apparatus that is used in combination with first and second cannula and reseal flow connectors includes a generally cylindrical and hollow shroud abutting the cannula hub in a hub pocket. The shroud surrounds a portion of the extending cannula. An interior thread on the inner surface of the shroud engages a resilient rolled-over exterior surface portion of the reseal connector in a self-threading manner.

In an alternative embodiment, the shroud is integrally manufactured with the cannula hub or in a further embodiment a separate securing shroud can be retrofitted to a cannula connector at the time of use.

Other features and advantages of the present invention will become readily apparent from the following detailed description, the accompanying drawings, and the appended claims.

BRIEF DESCRIPTION OF THE DRAWINGS

FIG. 1 is a partial side sectional view of a typical cannula connector inserted into a typical resealable septum connector.

FIG. 2 is a side sectional view of the securing apparatus according to the present invention showing a shroud having a double lead thread.

FIG. 3 is a side sectional view of an alternate embodiment of the present invention showing a shroud having a triple lead thread.

FIG. 4 is a side sectional view of a cannula and reseal connector secured by the securing apparatus of the present invention.

FIG. 5 is an enlarged view of FIG. 4 showing the rounded thread detail of the shroud.

FIG. 6 is a side sectional similar to FIG. 4 showing the securing apparatus of the present invention having an alternative rounded thread.

FIG. 7 is an enlarged view of FIG. 6 showing the alternative rounded thread detail.

FIG. 8 is a partial cross-sectional view of the securing apparatus according to the present invention showing an alternative embodiment that can be retrofit onto a cannula hub.

FIG. 9 is an enlarged view of FIG. 8 showing the mechanism to attach the cannula hub to the hub pocket of the shroud.

FIG. 9A is an enlarged view of the mechanism of FIG. 9 during initial assembly.

FIG. 10 shows a side sectional view of an integrally molded hub and shroud having a sharp cannula.

DESCRIPTION OF THE PREFERRED EMBODIMENT

Referring now to FIG. 1, an example of a first intravenous tubing set 12 in fluid communication with a second intravenous tubing set 13 is shown. The first tubing set includes a cannula connector 14. The cannula connector includes a cannula 16 which is preferably stainless steel and is secured by adhesive or other means to a molded rigid plastic cannula hub 18. A luer attachment 20 at the upstream end of the cannula connector allows the cannula hub to be attached to the first I.V. set. The downstream end of the cannula 16 can be sharp or blunt. As shown in FIG. 1, the cannula connector 14 is a LifeShield ® blunt cannula sold by Abbott Laboratories.

The second intravenous tubing set 13 includes a reseal connector 21 and is in downstream flow communication with the first connector. The second connector includes a rigid plastic tubular housing 22 and a resealable elastomeric septum 24. The septum 24 includes a plug portion 26 that is inserted into the interior of the rigid housing and an exterior rolled-over portion 28 which is folded down on the outside of the housing. The reseal is preferably made of a material such as a medical grade latex rubber that is sterilizable. The reseal may include an unpierced diaphragm portion that is first pierceable by a sharp cannula or may include a pre-pierced diaphragm portion such as the LifeShield pre-pierced reseal sold by Abbott Laboratories.

Due to the respective material properties of each flow connector, there is a frictional coefficient between the inserted cannula and the resilient reseal that creates a small axial securing force. This frictional force is large enough to maintain the flow connectors in axial flow communication during normal flow procedures. However, it is desirable to protect the flow connectors from accidental disconnection caused by larger disconnecting forces acting external to the tubing.

Referring now to FIG. 2, a preferred embodiment of a securing apparatus 40 is shown. The securing apparatus includes a shroud portion 42 and a hub pocket 44. The shroud is generally cylindrical and hollow, having an open end 46 and a closed end 48. While the downstream portion of the shroud near the opened end typically is cylindrical, the upstream portion 50 of the shroud near the closed end 48 preferably is slightly tapered. The taper is such that the diameter of the shroud decreases from near the axial middle of the shroud to a smaller diameter near the closed end. The taper is preferably about 5 degrees.

Key to this invention are the internal threads 52 that are located on the inner surface of the shroud 42. Further, the threads 52 are preferably located on the tapered portion 50 of the shroud. Thus the inner diameter of these internal threads tapers from the middle of the shroud to the closed end 48 of the shroud by about 5 degrees. As shown in FIG. 2, the threads are of constant height and the taper is a result of the taper of the inner surface of the upstream shroud portion 50.

Alternatively, the inner surface of the shroud housing could be made with a constant cylindrical diameter and the threads themselves could taper from a small height near the middle of the shroud to a larger height near the closed end, thus producing a tapering thread. This alternative is more complex to manufacture.

The closed end of the shroud 48 includes a coaxial opening 56 to the adjacent and oppositely extending hub pocket 44.

The internal thread shown in FIG. 2 is a double lead thread configuration. The inner diameter crests 60 of the threads are rounded and the root surface 62 between the crests is substantially flat. The lead-in 64 for each thread is substantially tangential. There are about 6 to 10 of each thread per inch, with 8 threads per inch being a preferred embodiment.

Shown in FIG. 3 is an alternative embodiment having a triple lead thread 66.

Shown in FIG. 4 is the connector apparatus of the present invention in use with a blunt cannula connector 14 and a prepierced rolled-over reseal connector 21. In this preferred embodiment the securing assembly 40 is attached to the cannula hub 18 by a sonic weld. This assembly is done during manufacturing prior to final packaging and sterilization of the connector assembly. (Alternatively, the cannula hub 18 is inserted into the hub pocket 44 and permanently secured by adhesive, sonic or other known bonding methods. The cannula and securing device is then sterilized and packaged for use.)

In use, the cannula 18 is inserted into the reseal 24 and the securing apparatus 40 is axially moved into contact with the reseal so that the leading threads 64 contact the resilient rolled-over exterior portion 28 of the reseal. Once this contact is made, the securing apparatus is rotated relative to the other connector such that the internal threads 52 self-thread onto the rolled-over exterior portion 28 of the resilient reseal. As shown in FIG. 5, the rounded shroud thread crests 60 will continue to thread onto the resilient exterior portion 28 of the reseal. The thread height and root surface 62 are dimensioned so that the resilient material of the reseal does not bind up in the threads and frictionally prevent further rotation of the threads. (If a flexible shrink wrap band is used to hold the elastomeric reseal onto the connector housing, the threads will continue to rotate onto the flexible shrink wrap band.)

The axial force necessary to pull the cannula 18 from the reseal 24 is increased from a minimal force (less than 2 pounds) to a force (in the approximate range of 5 to 15 pounds) which is sufficient to handle most accidental disconnection situations.

FIG. 6 shows an alternative rounded thread crest configuration, the details of which are shown in FIG. 7. Rather than the symmetrically rounded thread crest 60 shown in FIG. 4 and 5, the thread 70 is tapered primarily in the direction opposite to the thread travel. This configuration has been found beneficial in helping the thread crest to continue to self-thread from the resilient rolled-over portion 28 of the reseal over the shrink wrap band 72 as shown in FIG. 7. Further, FIG. 6 shows a cannula hub 18 adhesively bonded at 74 to the hub pocket 76.

FIG. 8 shows another embodiment of the securing apparatus that can be assembled to the cannula at the time of use. The cannula connector 14 and the securing shroud 78 are packaged and distributed separately. As shown in FIG. 9, the hub pocket 44 includes a one-way biting washer 80 having a flexible inner annular perimeter. The washer or any similar one-way axial attaching mechanism allows the securing shroud 78 to be retrofit onto the hub 18 of any cannula connector at the time of use when there is concern about accidental IV tube disconnection. FIG. 9A shows the annular washer 80 in the preassembly hub pocket 44 prior to the pocket end 82 being swaged over the washer.

FIG. 10 shows an integrally molded shroud and connector embodiment 86 of the invention. The cannula is insert molded or bonded to the hub of the integral shroud and connector during manufacture and the device requires no further assembly. Also illustrated in FIG. 10 is a sharp cannula 88 that is wholly contained within the shroud. Thus the shroud portion 42 functions both as a securing apparatus and a needle protecting apparatus. Alternatives of this embodiment would include a sharp needle cannula that extends beyond the shroud or a blunt cannula wholly contained within the shroud to protect the blunt cannula from touch contamination.

The preferred material of the shroud and/or integral shroud and connector is polypropylene or polycarbonate. These materials are readily moldable, and have a low coefficient of friction relative to the resilient elastomer used for the reseal 24. Thus the threads of the shroud cannot slide or be axially pulled off of the reseal by accident but require reverse rotation to disengage.

Another advantage of the tapered threads on the inner surface of the shroud of the present invention in addition to being self threading is that the tapering of the threads compensates for various stopper dimensions and various dimensional tolerances in like-type stoppers.

In operation, the securing apparatus of the present invention can be readily engaged and disengaged from tubular reseal connectors of the rolled-over reseal type.

A further advantage of the present invention is that the securing apparatus can be economically manufactured by a injection molding process. The internal threads 52 can be economically produced by an unscrewing core molding process.

An additional advantage of the securing apparatus of the present invention is that the securing apparatus can be reused for multiple connections. Likewise, the reseal septum can be reused since the rounded, non-cutting threads won't damage the exterior rolled-over portion of the reseal.

A final advantage is that the shroud portion provides protection for the exposed reseal surface of the second connector from touch contamination.

While several embodiments of the invention have been described, modifications within the scope of the present invention will be readily apparent to one of ordinary skill in the art. For example, the securing apparatus of the present invention may be used with any of the known fluid flow connectors such as sharp needles and unpierced reseals although the connector shown in the disclosed embodiments are primarily disclosed with respect to blunt cannula and prepierced reseals. All such modifications are intended to be covered by scope of the accompanying claims.

We claim:

1. An axial securing apparatus for use with an associated male fluid flow connector of the type having a cannula coaxially extending from a hub and an associated female fluid flow connector of the type having a resilient reseal with a rolled-over exterior surface portion, wherein the cannula of the male connector is axially inserted in the reseal of the female connector for fluid flow communication, the securing apparatus comprising;

a generally hollow cylindrical member having a first open end, a second open end, and a flange extending radially inward at a position between the first and second open ends, the first open end and the flange defining a hub pocket and the second open end and the flange defining a shroud portion oppositely extending from the hub pocket;

the hub pocket constructed and arranged so that the cannula hub of the male fluid flow connector fits in the first open end of the hollow member and is secured by attaching means so that the cannula extends through the flange into the opposed shroud portion;

the shroud portion constructed and arranged to have an inner cylindrical surface for threadingly receiving the exterior surface portion of the reseal of the female fluid flow connector; and threaded means on the inner cylindrical surface of the shroud portion for threadingly engaging the resilient rolled-over exterior surface portion of the reseal, the interior threaded means constructed to taper from a first diameter at the open end of the shroud portion to a second smaller diameter at the radial flange of the shroud portion and further constructed so that the interior threaded means has rounded crest portions and flat root portions.

2. The securing apparatus of claim 1 wherein the interior thread is a multiple lead thread.

3. The securing apparatus of claim 2 wherein the multiple lead thread is a double thread.

4. The securing apparatus of claim 1 wherein the thread has a tangential thread lead-in.

5. The securing apparatus of claim 1 wherein the thread lead is in the range of 6 to 10 threads per inch.

6. The securing apparatus of claim 1 wherein the generally cylindrical shroud has a taper of about 5 degrees on each side.

7. The securing apparatus of claim 1 wherein the hub pocket includes a center opening in the radially inward extending flange.

8. The securing apparatus of claim 7 wherein the attaching means is a sonic weldment of the hub pocket and the cannula hub.

* * * * *